United States Patent [19]

Boehme et al.

[11] Patent Number: 4,904,821
[45] Date of Patent: Feb. 27, 1990

[54] METHOD OF PREPARING PERACETIC ACID

[75] Inventors: Georg Boehme; Willi Hofen, both of Rodenbach, Fed. Rep. of Germany; Guenther Prescher, Larchmont, N.Y.; Rainer Siegmeier, Bad Homburg, Fed. Rep. of Germany

[73] Assignee: Degussa Aktiengesellschaft, Frankfurt, Fed. Rep. of Germany

[21] Appl. No.: 206,488

[22] Filed: Jun. 14, 1988

[30] Foreign Application Priority Data

Jun. 22, 1987 [DE] Fed. Rep. of Germany ....... 3720562

[51] Int. Cl.⁴ ............................................ C07C 179/10
[52] U.S. Cl. ...................................................... 562/6
[58] Field of Search ......................... 260/502 R; 562/6

[56] References Cited

FOREIGN PATENT DOCUMENTS 2141157 2/1973 Fed. Rep. of Germany ... 260/502 R
949094 2/1964 United Kingdom ............ 260/502 R

*Primary Examiner*—Bruce Gray
*Attorney, Agent, or Firm*—Beveridge, DeGrandi & Weilacher

[57] ABSTRACT

In order to safely prepare peracetic acid in an organic solvent, the bottom is maintained in a certain stationary state during the preparation of aqueous peracetic acid, whereupon the vapor current of peracetic acid, acetic acid and water is absorbed with an organic phosphate with 3–30 carbon atoms. The solution obtained in this manner can be transferred by means of desorption with a low-boiling compound, e.g. an alkyl ester, into this lower-boiling solvent.

9 Claims, 1 Drawing Sheet

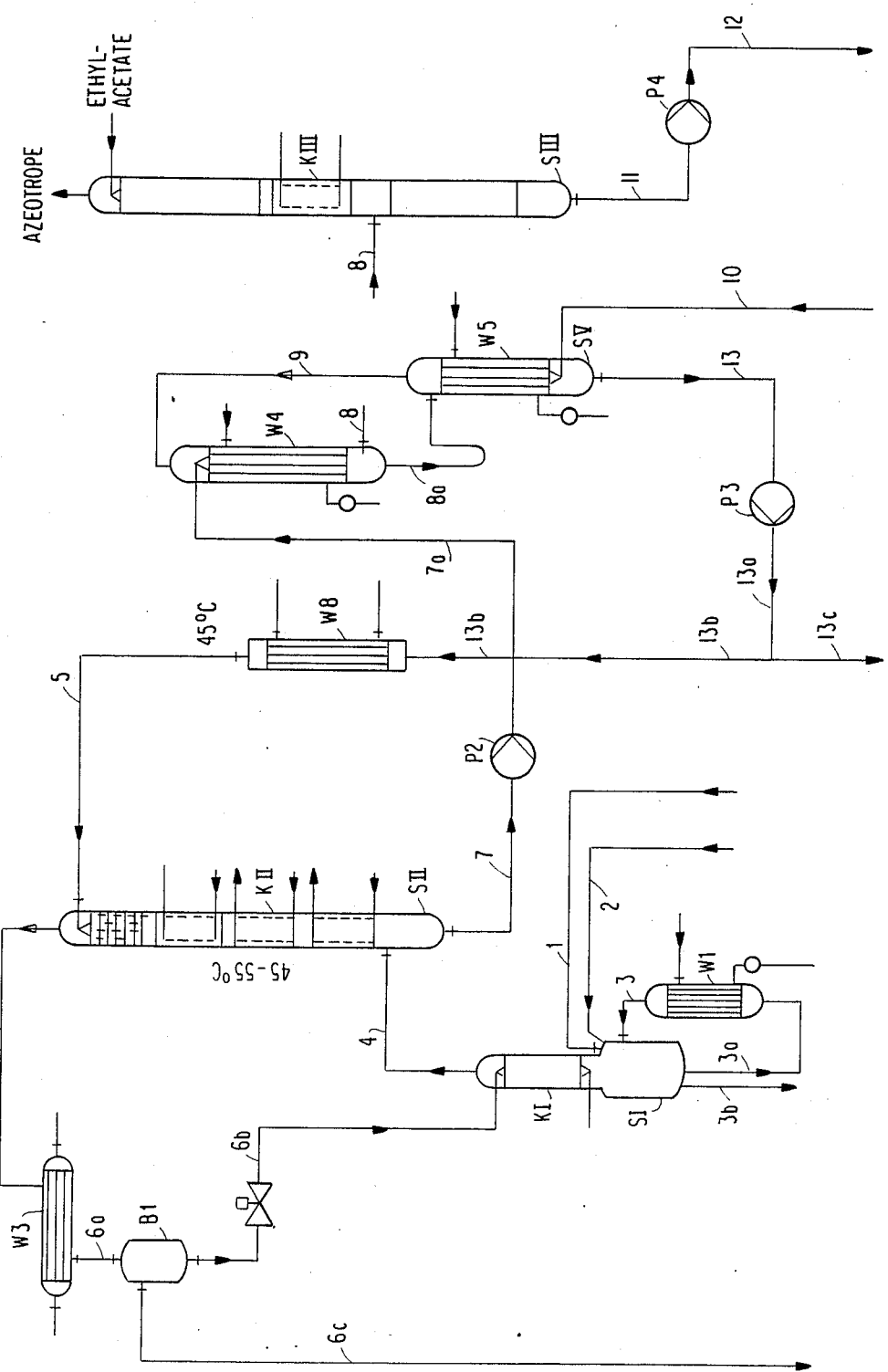
FIGURE

METHOD OF PREPARING PERACETIC ACID

INTRODUCTION AND BACKGROUND

The present invention relates to the method of preparing peracetic acid.

One of the best-known oxidation agents is peracetic acid, especially for the preparation of epoxides or lactones from ketones via the Baeyer-Villiger reaction.

Peracetic acid is generally prepared in a classical manner by reacting acetic acid with hydrogen peroxide in the presence of an acidic catalyst, usually sulfuric acid. More or less pure aqueous solutions of peracetic acid accumulate thereby, depending on the type of performance, such as, for example, the so-called equilibrium peracetic acid consisting of approximately 40–42% peracetic acid, 37–40% acetic acid, 10–14% water, 4–6% hydrogen peroxide and 0.5–1% sulfuric acid. ("Ullmann's Enzyklopädie der technischen Chemie", 3d edition, vol. 13, p. 254)

Very pure aqueous solutions are obtained if a reaction mixture is used which contains, in addition to water and the acidic catalyst, more than 1 mole hydrogen peroxide per mole acetic acid and if the peracetic acid is distilled off under reduced pressure with water, cf. loc. cit., Supplementary Volume, 3d edition, page 181. These very pure solutions can be converted by means of azeotropic entrainer agent distillation into water-free organic peracetic acid solutions, cf. loc. cit. and DE-PS 11 65 576.

A water-free, organic solution of peracetic acid can also be obtained by azeotropically removing the water by means of the simultaneous presence of an organic solvent which forms an azeotrope with water in the reaction of hydrogen peroxide and acetic acid in the presence of an acidic catalyst, cf. Ullmann, Supplementary Volume, loc. cit.

However, there are also known industrial safety risks involved in the preparation of organic percarboxylic acid solutions. For this reason, the attempt was made to obtain the corresponding organic solutions by means of the direct extraction of aqueous mixtures of percarboxylic acid, which solutions were azeotropically dewatered by the addition of an entrainer agent. Suitable extraction agents were aliphatic, cycloaliphatic and aromatic hydrocarbons as well as chlorinated hydrocarbons, cf. DE-OS 21 45 603. Hydrogen peroxide was added as a 30 to 90% by weight, preferably as 45 to 70% by weight aqueous solution in excess over the carboxylic acid, preferably in highly concentrated, aqueous form.

Phosphoric ester, preferably trialkyl phosphates, were also used as extraction agents and the extracts obtained were then desorbed with alkyl esters of lower carboxylic acids. The percarboxylic acids used were 10–80, preferably 20–60% by weight aqueous solutions, cf. U.S. Pat. No. 3,829,216.

A moment of danger was seen only in the fact that an organic solvent was present in addition to hydrogen peroxide, percarboxylic acid and acidic catalyst and the only attempt made was to avoid this combination. It turned out, however, that the moment of danger also occurred without the presence of an organic solvent. For this reason, in particular the molar ratio of hydrogen peroxide to carboxylic acid used was set at certain values before the reaction was started. It also turned out that the safety of the system did not, as assumed, remain continuously constant after a certain value but rather that a distinct safety gap occurred within the ranges of this molar ratio used, cf. DE-OS 25 19 299 and 25 19 300. The weight ratio of hydrogen peroxide to water also played a part in this process.

SUMMARY OF THE INVENTION

The present invention therefore has the object of providing a method for the preparation of peracetic acid and its extraction in an organic solvent in a manner which is unobjectionable from the standpoint of industrial safety.

It was found that this and other objects can be achieved if the reaction is performed in a simple distillation apparatus in such a manner that hydrogen peroxide and acetic acid in a molar ratio of 1 to 2:1 and hydrogen peroxide in a 30–35% by weight aqueous solution are placed in the bottom of the apparatus, i.e. the distillation zone, before the start of the reaction. The concentration of sulfuric acid is adjusted to 20–30% by weight in relation to the entire solution. This state of the above-defined quantities used is maintained in the bottom of the column in a stationary manner and the reaction is performed at temperatures of 55° to 70° C. and system pressures of 100–200 mbars. Thus, no agitation implement is used. As a result of the reaction, a vapor phase of peracetic acid, acetic acid and water is removed from the apparatus. This vapor phase is then conducted in a countercurrent manner into an absorption column to contact an organic phosphate with 3–30 carbon atoms which takes up the portion of peracetic acid and acetic acid. As a result thereof a solution of peracetic acid and acetic acid is obtained in the phosphate involved while the non-absorbed water vapor is taken off over head and leaves the system.

BRIEF DESCRIPTION OF DRAWING

The process of the present invention will be further understood with reference to the drawing which shows a schematic of a simple distillation apparatus.

DETAILED DESCRIPTION OF INVENTION

The term "simple distillation apparatus" refers to the "distillation zone" and denotes all apparatuses which are known for a simple or straight distillation such as e.g. boilers, evaporation flasks, bottom evaporators and which are preferably connected to a condenser or dephlegmator. Even columns with or without dephlegmator, which are preferably designed as a plate column, can be used. The apparatuses known in absorption technology can be considered as customary absorption columns. The system comprising the reaction and the absorption is preferably run at temperatures of 45°–65° C. If the absorption is run, for example, at 45°–55° C., it is possible, via the absorption equilibrium, to obtain a 23% by weight solution of peracetic acid in tributyl phosphate in bottom S II, as shown in the drawing. The higher the absorption temperature, the lower the concentrations of peracetic acid in bottom S II.

The reaction part of the system is operated in such a manner that a weight ratio of peracetic acid to acetic acid of 2 to 3:1, preferably 2.5 to 3:1, is adjusted in the vapor phase, the balance is water. The preferred composition of the vapor corresponds to 45–47% by weight peracetic acid, 14–17% by wt. acetic acid, remainder water.

Suitable organic phosphates for purposes of the invention are those with 3–30 carbon atoms such as trisubstituted phosphates, namely either alkyl, cycloalkyl or aryl phosphates, which can also be added as mixtures. Useful phosphates are e.g. trialkylesters of phosphoric acid with alkyl containing 1-10 C atoms as well as tricyclohexyl phosphate or triphenyl phosphate, tricresyl phosphate, diphenylcresyl phosphate. Trimethyl, triethyl, tributyl and tiroctyl phosphate are preferred. Mixtures can be used.

Since only as much water can be distilled out of the system as corresponds to the portion of hydrogen peroxide solution introduced and the reaction water, any commercially available solution, e.g. a 50-70% solution, can be fed in for the continuous reaction, independently of the usage of a 30-35% by wt. aqueous hydrogen peroxide solution placed initially in the receiver.

If the peracetic acid is not to be used as solution in a phosphoric ester, it is possible to transfer the peracetic acid from the phosphate into another organic solvent such as e.g. aliphatic esters in a customary manner. These solvents must be stable against oxidations under customary desorption conditions and must be easy to separate in a distillative manner from acetic acid. Methyl to propyl acetates are preferred. Aromatic hydrocarbons, e.g. benzene, or chlorinated hydrocarbons, even in a mixture with esters, can also be used. In general mixtures can be used.

The desorption of peracetic acid and acetic acid from the phosphate solution can be performed in a known manner by introducing the vaporous second solvent. The desorbates produced can, if desired, be completely dewatered by azeotropic distillation.

The method of the invention, which is preferably performed in a continuous manner, will now be explained in more detail with reference made to the drawing. The numerical values contained in the description of this drawing are given solely by way of example.

Illustratively, the distillation apparatus used is a bottom column K I (with dephlegmator set on top). Hydrogen peroxide and acetic acid (AC) in a molar ratio of 1.5:1 are placed in bottom S I of the column before the start of the reaction. A 40-50% by wt. hydrogen peroxide is used. The weight ratio of hydrogen peroxide to water is adjusted to 0.54 by the addition of water. This corresponds to a 35% by wt. hydrogen peroxide solution. Sulfuric acid is added to the mixture in such an amount that its concentration in the mixture is e.g. 25-30% by wt.

This bottom mixture placed in a receiver before the start of the reaction is maintained constant during the duration of the reaction to such a degree by using a system pressure of 100-150 mbars, a reflux ratio of 0.3-0.5 and the continuous addition of 40-50% by weight hydrogen peroxide solution and acetic acid in a feed ratio (weight ratio) of 0.7 to 0.8:1 that the quantities of molar quotient ($H_2O_2/AC$) and weight ratio ($H_2O_2/H_2O$) calculated for use before the start of the reaction remain preserved. The bottom temperature is e.g. 60° C. and is maintained with the aid of forced-circulation reboiler W 1 via lines 3, 3a.

A vapor current is obtained under these conditions which consists of approximately 47% by wt. peracetic acid (PAC), approximately 16% by wt. acetic acid, approximately 37% by wt. water and less than 0.1% by wt. hydrogen peroxide and is conducted via line 4 into the lower part (bottom S II) of absorption column K II. An organic phosphate, e.g. tributyl phosphate (TBF) is added via line 5 at the column head and conducted in countercurrent flow to the rising vapor current.

The phosphate absorbs both the peracetic acid and the acetic acid from the vapor current but only slight amounts of water (they correspond at a maximum to the solubility of water in tributyl phosphate). Almost the entire amount of water present in the vapor current leaves absorption column K II via line 6, is condensed in condenser W 3, passes via line 6a into separator B 1 and is removed from it via line 6c. A small partial amount is fed as reflux to column K I in order to retain hydrogen peroxide in bottom S I (via line 6b).

Bottom S II of absorption column K II contains, as stated, the peracetic acid and acetic acid, absorbed in tributyl phosphate. The absorption agent should always be used in such an amount that practically no peracetic acid and acetic acid escape together with the water vapor at the head of column K II in a single passage of the vapor current from distillation apparatus K I at a given temperature and pressure. This can be readily determined by a preliminary test as will be apparent to those skilled in the art.

In the instant case given by way of example a 23% by wt. solution of peracetic acid in addition to 7% by wt. acetic acid in tributyl phosphate was obtained with tributyl phosphate at a temperature of 45°–55° C. and a pressure of 100-150 mbars (since the columns K I and K II form a coherent system). The stable solution of peracetic acid in tributyl phosphate obtained in this manner can be used in this form. It is removed from bottom S II (not shown).

However, if peracetic acid is to be used in another solvent, e.g. in an aliphatic ester such as ethyl acetate, then the solution obtained in tributyl phosphate is conducted via line 7, pump 2 and line 7a to the head of evaporator system W 4 and W 5, which illustratively consists of falling-film evaporators, and desorbed with the aid of vapors of ethyl acetate introduced via line 10 which are introduced via W 5 and line 9 into W 4. The vapor currents of the desorption system pass via line 8 into column K III. The tributyl phosphate freed to a large extent of peracetic acid and acetic acid passes via line 8a from W 4 to W 5 and leaves bottom S V via line 13. The tributyl phosphate running out of S V is preferably almost completely freed of dissolved ethyl acetate by means of water vapor stripping (not shown).

The vapor current of peracetic acid and acetic acid in ethyl acetate is removed, as stated, in the bottom of W 4 via line 8 and can also be optionally dewatered in column K III by formation of an azeotrope from the slight residue of water with a part of the ethyl acetate which is removed via the head of column K III. The heteroazeotropic mixture of water and ethyl acetate distilled off during the dewatering is condensed in a customary manner, water is removed and ethyl acetate returned (not shown). Otherwise, it can be directly condensed.

A practically water-free solution of peracetic acid and acetic acid in ethyl acetate is removed from bottom S III of column K III via line 11, pump 4 and line 12. A 23% by wt. solution of peracetic acid in ethyl acetate was obtained at a column pressure of 300 mbars which also contained 7% by wt. acetic acid in addition. Thus, the entire amount of peracetic acid present in tributyl phosphate can be transferred into ethyl acetate.

Very different concentrations of peracetic acid in trialkyl phosphate or another solvent (by desorption of the trialkyl phosphate solution) can be obtained, according to the conditions of the "K I and K II" system. The tributyl phosphate, freed to a great extent of peracetic acid, that is in the exemplary instance down to 0.02% by wt. peracetic acid, and of acetic acid, that is, down to 1.5% by wt. acetic acid, collects in bottom S V of evaporator W 5, is returned via line 13, pump 3 and line 13a and 13b into cooler W 8 and cooled off there to the absorption temperature of e.g. 45° C. Thereafter, the tributyl phosphate passes back to the head of column K II (via line 5).

A partial current of tributyl phosphate is periodically removed via line 13c and cleaned, in which manner the amount of accumulating impurities is held to a low level.

In order to keep the accumulation of impurities in bottom S I low, a low removal rate must be generated via line 3b, e.g. 2% by wt. in relation to the feed of hydrogen peroxide, water and acetic acid, which can be returned after cleaning to K I (not shown).

The technical advance of the method of the invention resides in the absolutely safe performance of the method since the hydrogen peroxide concentration is controlled and held from the beginning to a low level during the preparation of peracetic acid in the bottom of the preparation apparatus and is held at this level during the reaction. In this manner, the dangerous occurrence of safety gaps is completely avoided. This safety is increased even more by processing the vapor current containing water vapor by means of absorption in an organic solvent, which makes it impossible for a condensed, high-percentage aqueous phase of peracetic acid to be produced.

The solutions of peracetic acid in alkyl phosphates obtained in accordance with the method of the invention are remarkably stable, even at rather high temperatures. Thus, the decomposition rate of a solution containing 23% by wt. peracetic acid in addition to 7% by wt. acetic acid is only 0.5–0.8% by weight/h at 55° C. in tributyl phosphate.

Another advantage of the peracetic acid solutions prepared according to the invention in alkyl phosphates resides in the low evaporation speed of these phosphates, so that no concentration of the solutions due to evaporation of the solvent can occur.

Further variations and modifications of the present invention will become apparent to those skilled in the art and are intended to be ecompassed by the appended claims.

German priority application P 37 20 562.5-42 herein by reference.

We claim:

1. A method of preparing peracetic acid in organic solution in a continuous manner comprising hydrogen peroxide and acetic acid in the presence of sulfuric acid as reactants in a simple distillation zone in such a manner that (a) hydrogen peroxide and acetic acid are in a molar ratio of 1 to 2:1 and (b) hydrogen peroxide is in a 30–35% by weight aqueous solution whereby the weight ratio of hydrogen peroxide to water is between 0.43 and 0.54, and the reactants are placed in the bottom of said distillation zone before the start of said reaction, (c) the concentration of sulfuric acid is adjusted to 20–30% by weight in relation to the entire solution, maintaining this (a)(b)(c) mix state of the above-defined reactants in the bottom of the column in a stationary manner so as to remain constant during the reaction, carrying out the reaction at temperatures of 55° to 70° C, and at system pressures of 100–200 mbars, removing a vapor phase of peracetic acid, acetic acid and water from the distillation zone, conducting said zone vapor phase into an absorption zone in countercurrent contact with organic phosphate having 3–30 carbon atoms which takes up the portion of peracetic acid and acetic acid, thereby forming a solution of peracetic acid and acetic acid in the phosphate, and removing the non-absorbed water vapor.

2. The method according to claim 1, wherein said reactants are placed in a plate column with a dephlegmator set on top as a distillation zone.

3. The method according to claim 1, wherein hydrogen peroxide and acetic acid are placed in said zone before the start of the reaction in a molar ratio of 1.5:1, the weight ratio of hydrogen peroxide to water is adjusted to 0.54 and the concentration of sulfuric acid in the entire mixture is adjusted to 25–30% by wt.

4. The method according to claim 1, wherein the reaction is performed at a system pressure of 100–150 mbars, a reflux ratio of 0.3 to 0.5 and a continuous infeed of 40–50% by wt. aqueous hydrogen peroxide solution and acetic acid in a weight ratio of 0.7 to 0.8:1.

5. The method according to claim 1, wherein trisubstituted alkyl, cycloalkyl or aryl phosphates are used in the absorption zone.

6. The method according to claim 5, wherein trialkyl phosphate in which alkyl contains 1–10 carbon atoms is used.

7. The method according to claim 6, wherein trimethyl, triethyl, tributyl or trioctyl phosphate is used.

8. The method according to claim 7, wherein a solution of peracetic acid and acetic acid in tributyl phosphate is transferred by desorption with aliphatic esters into a solution of the said aliphatic esters.

9. The method as claimed in claim 8, wherein said aliphatic ester is ethyl acetate.

* * * * *